United States Patent
Schmucker et al.

(10) Patent No.: US 6,468,514 B2
(45) Date of Patent: Oct. 22, 2002

(54) METHOD OF PREPARING PARTICULARLY SKIN-COMPATIBLE COSMETIC OR DERMATOLOGICAL CLEANSING PREPARATIONS

(75) Inventors: Robert Schmucker; Martin Sugár, both of Hamburg (DE)

(73) Assignee: Beiersdorf AG, Hamburg (DE)

(*) Notice: Subject to any disclaimer, the term of this patent is extended or adjusted under 35 U.S.C. 154(b) by 0 days.

(21) Appl. No.: 09/738,250

(22) Filed: Dec. 15, 2000

(65) Prior Publication Data

US 2002/0028188 A1 Mar. 7, 2002

(30) Foreign Application Priority Data

Dec. 16, 1999 (DE) .......................... 199 60 766

(51) Int. Cl.[7] .............. A61K 7/40; A61K 7/48; A61K 7/50; C11D 11/00; C11D 1/86
(52) U.S. Cl. ............. 424/70.19; 424/401; 424/70.21; 424/70.24; 514/975; 514/846; 514/887; 514/773; 514/801; 514/828; 514/847; 514/945; 510/155; 510/108; 510/130; 510/135; 510/152
(58) Field of Search ............. 424/401, 70.19, 424/70.21, 70.24; 514/975, 773, 801, 828, 846, 847, 887, 945; 510/155, 108, 130, 135, 152

(56) References Cited

U.S. PATENT DOCUMENTS 5,556,628 A * 9/1996 Derian et al. .............. 424/401
5,994,281 A * 11/1999 He et al. .................... 510/152

OTHER PUBLICATIONS

International Cosmetic Ingredient Dictionary and Handbook, 1997, The Cosmetic, Toiletry, and Fragrance Association, vol. 2, pp. 1673–1690.*

* cited by examiner

Primary Examiner—Frederick Krass
Assistant Examiner—Clinton Ostrup
(74) Attorney, Agent, or Firm—Norris McLaughlin & Marcus

(57) ABSTRACT

The use of one or more cosurfactants (surfactant B) in a mixture with one or more surfactants different from surfactant B (surfactant A) for reducing the binding of surfactant A to the surface of the skin.

16 Claims, 2 Drawing Sheets

Figure 1:
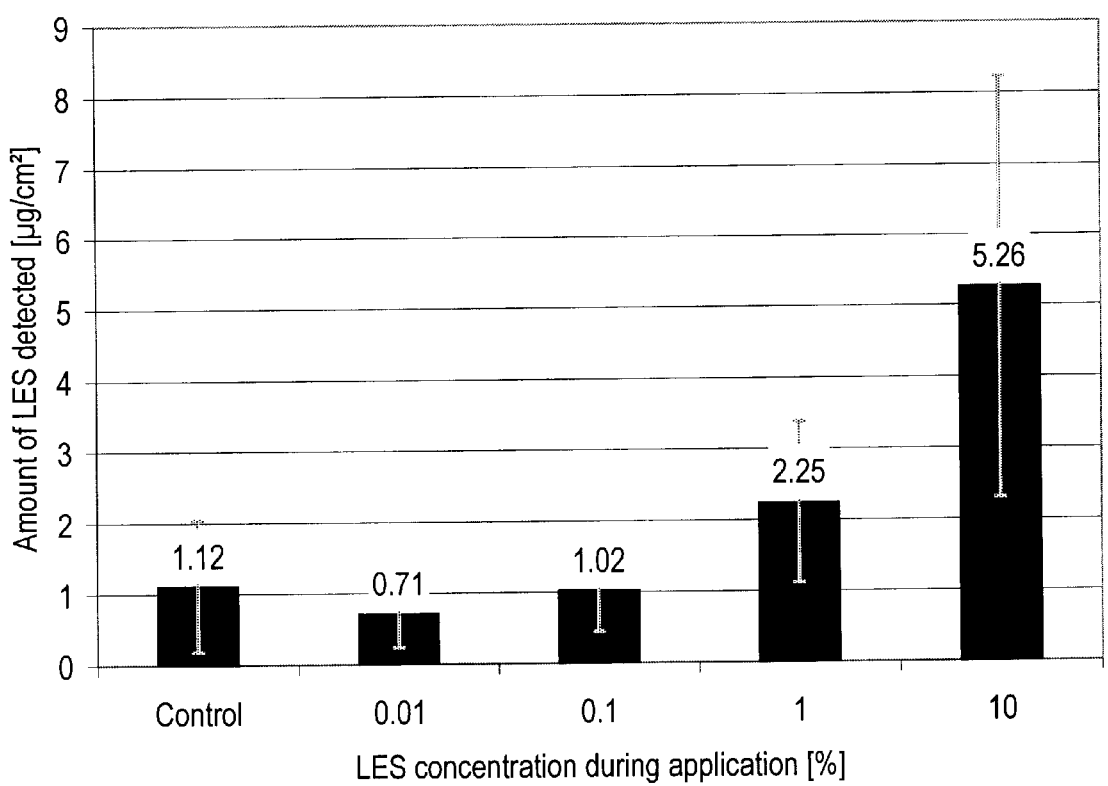

METHOD OF PREPARING PARTICULARLY SKIN-COMPATIBLE COSMETIC OR DERMATOLOGICAL CLEANSING PREPARATIONS

The present invention relates to a method of preparing particularly skin-compatible cosmetic or dermatological cleansing preparations.

Preparations of this type are, for example, foam baths and shower preparations, solid and liquid soaps or co-called "syndets" (synthetic detergents), shampoos, handwash pastes, personal hygiene washing compositions, special cleansers for small children and the like.

In a particular embodiment, the present invention relates to cleansing preparations for use as shower preparations, bath preparations, body cleansing and face cleansing.

Preparations of this type are also known per se. They are essentially surface-active substances or substance mixtures supplied to the consumer in a variety of preparations. Preparations of such type are generally distinguished by a greater or lesser water content, but can also, for example, be in the form of concentrate.

Even simple bathing in water without the addition of surfactants will initially cause the horny layer of the skin to swell, the degree of this swelling depending, for example, on the bathing time and temperature. As well as water-soluble substances, e.g. water-soluble constituents of dirt, substances endogenous to the skin which are responsible for the water-binding capacity of the horny layer are also washed off or out. In addition, as a result of surface-active substances endogenous to the skin, fats in the skin are also dissolved and washed out to a certain degree. After the initial swelling, this causes a subsequent significant drying-out of the skin, which may be further intensified by washing-active additives.

In healthy skin, these processes are generally of no consequence since the protective mechanisms of the skin can readily compensate for such slight disturbances to the upper layers of the skin. However, even in the case of nonpathological deviations from the norm, e.g. as a result of wear damage or irritation caused by the environment, photodamage, aging skin etc., the protective mechanism of the surface of the skin is impaired. In some circumstances it is then no longer able to fulfill its role by itself and must be regenerated by external measures.

The object of the present invention was therefore to remedy these shortcomings of the prior art. It was further an object of the invention to provide bath or shower preparations which on the one hand have a high care action, without, on the other hand, the cleansing action becoming inferior.

Surface-active substances, the best known being the alkali metal salts of higher fatty acids, i.e. the classical "soaps"—are amphiphilic substances which are able to emulsify or solubilize organic nonpolar substances in water.

These substances not only flush dirt from the skin and hair, they irritate skin and mucous membranes to a greater or lesser extent depending on the choice of surfactant or surfactant mixture.

One of the most commonly used surfactants for cosmetic compositions throughout the world is sodium lauryl ether sulfate. Although an excellent washing-active agent with good foaming ability, in higher concentrations it has an irritative effect on skin and mucous membranes.

As more recent investigations show, the irritancy potential of sodium lauryl ether sulfate is at least partially promoted by the fact that this substance binds to the surface of the skin where it forms a certain reservoir. Studies suggest that lauryl ether sulfate from this reservoir penetrates into the deeper layers of the skin, where it can then cause uncontrolled secondary reactions, which harbor an increased risk of irritation.

Commercially available sodium lauryl ether sulfate (=sodium polyoxyethylene lauryl sulfate, according to INCI nomenclature: "Sodium laureth sulfate"; CAS No.1335–72–4), like most raw materials used in cosmetics, is not a pure substance, but, depending on the preparation, is more likely a mixture of substances, the structures of which conform to the general formula

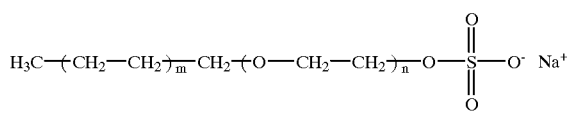

where n assumes numbers from 0 to 10 and m assumes numbers from 4 to 6. The lauryl ether derivative which predominates in the commerical products and gives them their name has m=5, n=2–3. Commercial products are, for example, Texapon® N 25, Texapon® N 40, Texapon® N 70 and Texapon® N 103 from Henkel KGaA.

There are, however, also other lauryl ether sulfates which have, as counterion, for example, unsubstituted ammonium ions or ammonium ions substituted by alkyl groups or hydroxyalkyl groups, but also magnesium and such like.

However, because of the ready availability, the acceptable price and the excellent washing properties of sodium lauryl ether sulfate, it will not be possible in practice to dispense with this substance entirely in the foreseeable future. Although lauryl ether sulfate-free preparations are known and entirely advantageous, they are characterized by other performance- or preparation-related or economic disadvantages.

The long-term application (for example longer than 1 hour) or repeated short-term application of anionic surfactants can lead to a reduction in skin moisture or to an increase in the transepidermal water loss (TEWL).

It is known per se to use sodium lauryl ether sulfate in combination with other surfactants as washing-active agent. The person skilled in the art who would then like to increase the skin compatibility of such preparations then replaces some of the sodium lauryl ether sulfate with milder surfactants. However, a reduction in foaming and/or cleansing performance usually has to be accepted as an undesired side effect. The aim was therefore to remedy this shortcoming.

In the attempt to increase the compatibility of lauryl ether sulfate on the basis of scientific laws without replacing the surfactant with other, better tolerated surfactants (=cosurfactants), the person skilled in the art is faced with the following, as yet unresolved, contradiction:

The skin compatibility of surfactants correlates with the monomer concentration/CMC of the surfactants. It does not increase further at concentrations above the CMC.

Imokawa G, Mishima Y. *Contact Dermatitis.* 1979: 5: 357

Breuer M M. *J Soc. Cosmet. Chem.* 1979: 30: 41

The degree of skin damage increases with increasing surfactant concentration—even above the CMC.

Wilhelm K P, Surber C, Maibach H I. *Arch. Dermatol. Res.* 1989: 281: 293–295.

Because of this contradiction, it was not clear to the developer which laws can be used to prepare a milder formulation of a given surfactant system—in this case lauryl ether sulfate.

In various publications it has been speculated that there is a connection between the skin reaction and the adsorption of surfactants on the skin. However, all of the investigations relating to the adsorption of surfactants on the skin have been carried out either in vitro on substances with limited similarity to the human skin (callous powder, skin powder, isolated human or mammal Stratum corneum)

Dominguez J G, Parra J L, Infante M R, Pelejero C M, Balaguer F, Sastre T. *J Soc. Cosmet. Chem.* 1977: 28: 165

Garret H E. *Trans. of St. John's Hosp. Dermatol. Soc.* 1965: 51: 166

Faucher J A, Goddard E D. *J Soc. Cosmet. Chem.* 1978: 29: 323

Gibson W T, Teall M R. *Fd Chem. Toxic.* 1982: 21: 581 ex vivo (excised human or mammal skin)

Fullerton A, Broby-Johansen U, Agner T. *Contact Dermatitis.* 1994: 30: 222 or in vivo using inadequate, irrelevant, due to being application-remote, or nonvalidated methods (indirect dyeing methods, extraction with water or acetone)

Imokawa G, Mishima Y. *Contact Dermatitis.* 1979: 5: 357.

Adsorption measurements carried out under equilibrium conditions (long-term application) are of no relevance for application conditions (showering). Measurements described in the literature do not therefore adequately reflect the application situation and therefore produced irrelevant results.

At the 2$^{nd}$ Scientific Conference of the Asian Societies of Cosmetic Scientists, 1995, in Seoul, a paper entitled "Development of High-Safety Facial Cleansers through Reduction of Cutaneous Surfactant Adsorption" was presented which dealt with a theme related to the present invention.

However, the "facial cleansers" are soap products which, however, are not intended to be the subject of our patent. Although soaps are also anionic surfactants, they can only develop their surface-active action at a high pH. Upon contact with the skin, soaps can lose their basicity as a result of the buffering action of the skin and as a result lose their soap character. The synthetic detergents on which we focus do not have this peculiarity.

By virtue of this limitation, soaps exhibit unique characteristics and, when compared with synthetic detergents such as lauryl ether sulfate or SLS, are to be regarded as an independent product class.

The method which we have developed for determining the adsorption of lauryl ether sulfate on the skin simulates a washing operation as occurs, for example, during daily showering:

Firstly, the inner sides of the forearms are divided into a number of test areas using insulating tape. The area to be treated is then wetted with approximately 50 ml of mains water (T=38±1° C.). The lauryl ether sulfate is then applied. Throughout the application period of 45 s, the test subject distributes the lauryl ether sulfate over the area using 2 fingers in uniform circular movements. At the end of the application period, the test area is rinsed with approximately 950 ml of mains water (T=38±1° C.) and carefully patted dry using a clean cellulose cloth. For the desorption, a plastic ring with an internal diameter of 25 mm is pressed firmly onto the inner side of the test subject's forearm. 1000 µl of a 1% Triton X-100 solution are then introduced into the ring. The tip of a round Teflon-coated spatula is then used to scrape the skin uniformly for 1 min. This leads to suspension of corneocytes. To work up the samples for analysis, the samples are centrifuged and 800 µl of the supernatant are drawn off. The supernatant is analyzed with regard to its lauryl ether sulfate content using ion-pair chromatography. The effectiveness of the desorption method described is 79%, i.e. 79% of the amount of lauryl ether sulfate actually present on the skin are included.

The results of the experiments for the adsorption of lauryl ether sulfate show that sodium lauryl ether sulfate adsorbs/binds to the surface of the skin during washing operations under use conditions.

Surprisingly, the amount of surfactant adsorbed to the surface of the skin under use conditions further increases even above the maximum achievable monomer concentration (CMC). FIG. 1 shows the adsorbed amount of lauryl ether sulfate as a function of the lauryl ether sulfate concentration. The CMC of the lauryl ether sulfate used is between 0.01 and 0.1% by weight.

The object of the present invention was therefore to remedy the shortcomings uncovered.

Surprisingly, and herein lies the basis of the solution, the shortcomings are overcome according to the invention through the use of one or more cosurfactants (surfactant B) which do not correspond to the surfactant sodium lauryl ether sulfate in a mixture with the surfactant sodium lauryl ether sulfate for reducing the binding of surfactant A to the surface of the skin.

The invention further relates to the use of one or more cosurfactants (surfactant B) for the preparation of mild washing-active cosmetic or dermatological preparations with a further content of one or more washing-active surfactants, which have a tendency to bind to the surface of the skin (surfactant A), which, when used, achieve a decrease in or prevention of the binding of surfactant A to the surface of the skin.

In a particular embodiment, the present invention relates to washing-active hair cosmetic preparations, commonly referred to as shampoos. In particular, the present invention relates to hair cosmetic active ingredient combinations and preparations for the care of the scalp.

Surprisingly and unforeseeable by the person skilled in the art, it has been found that the addition of cosurfactants to lauryl ether sulfate leads to a reduction in the amount of lauryl ether sulfate adsorbed on the skin. Skin compatibility studies carried out in parallel demonstrate the increased mildness of the products as a result of the addition of cosurfactants.

Table 1 shows the reduction in the adsorption of lauryl ether sulfate as a result of the addition of different cosurfactants to a lauryl ether sulfate solution.

TABLE 1

| Cosurfactant | Cosurfactant concentration | Effect on the adsorbed amount of lauryl ether sulfate | Significance |
|---|---|---|---|
| Sodium lauroyl glutamate | 1.5% | Reduction by 31% | Yes |
| Disodium laureth sulfosuccinate | 3% | Reduction by 28% | Yes |
| Sodium lauroyl sarcosinate | 3% | Reduction by 23% | Yes |
| Sodium cocoamphoacetate | 3% | Reduction by 27% | Yes |
| Cocamidopropylbetaine | 3% | Reduction by 31% | Yes |
| Decyl glucoside | 5% | Reduction by 29% | Yes |
| Lauric acid, pH9 | 1% | Reduction by 15% | Yes |

This result is all the more surprising since the addition of one or more cosurfactants leads to an increase in the active content of surfactants in the formulation. The person skilled in the art would expect a reduction in skin mildness as a result of this increase in concentration.

Surprisingly, the opposite result was found: the increase in the overall surfactant concentration led to an increase in the mildness of the products.

A further embodiment of the present invention relates to the use of one or more cosurfactants (surfactant B) in a mixture with one or more surfactants which differ from surfactant B (surfactant A) for decreasing the binding of surfactant A to the surface of the skin.

Figure 2:
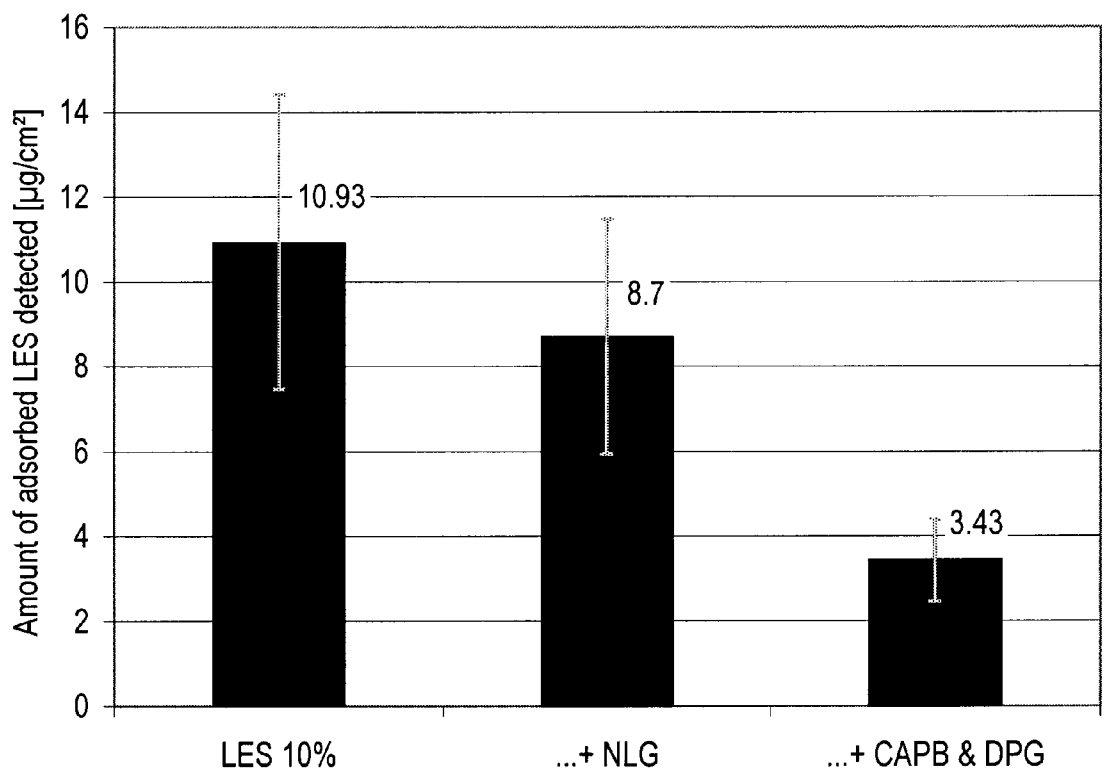

FIG. 2 shows the reduction in the adsorption of lauryl ether sulfate as a result of the addition of various cosurfactants to a lauryl ether sulfate solution. Here, LES means sodium lauryl ether sulfate. NLG means sodium lauroyl glutamate. CAPB means cocamidopropylbetaine. DPG means decyl polyglucoside.

For example, the present invention manifests itself in washing-active cosmetic or dermatological preparations comprising:

(a) more than 9.0% by weight of lauryl ether sulfate, (b) one or more anionic surfactants chosen from the group of N-acylamino acids and salts thereof, (c) other surfactants, such as cocamidopropyl betaine, decyl or dodecyl polyglucoside, disodium laureth sulfosuccinate, sodium lauroyl sarcosinate, trilaureth 4-phosphate, sodium cocoamphoacetate, disodium cocoamphoacetate, (d) less than 5.0% by weight of inorganic salts.

The present invention is also realized by washing-active cosmetic or dermatological preparations comprising:

(a) more than 9.0% by weight of lauryl ether sulfate, (b) more than 1.0% by weight, in particular more than 1.75% by weight of one or more anionic surfactants chosen from the group of N-acylamino acids and salts thereof, (c) less than 5.0% by weight of inorganic salts.

Surfactant B can advantageously be chosen from the group of N-acylamino acids and salts thereof, this surfactant or these surfactants being present in washing-active cosmetic or dermatological preparations in concentrations greater than 3.0% by weight, based on the total weight of the preparations, for reducing the attachment of lauryl ether sulfate to human skin during the washing operation or for removing lauryl ether sulfate from human skin.

It is known per se that N-acylamino acids and salts thereof are mild surfactants with a useful foaming action and good washing action (H. P. Fiedler, Lexikon der Hilfsstoffe für Pharmazie, Kosmetik und angrenzende Gebiete [Lexicon of auxiliaries for pharmacy, cosmetics and related fields], 4$^{th}$ edition, p. 108, keyword "N-Acylglutaminsäure" [N-acylglutamic acid]).

The paper "Surface Active N-Acylglutamate: Preparation of Long Chain N-Acylglutamic Acid" (M. Takehara, I. Yoshimura, K. Takizawa, R. Yoshida; Journal of the American Oil Chemists' Society Vol.49, p.157 ff.) cites JP Patent 29 444 (1964), according to which acyl glutamates are said to alleviate skin irritations caused by other anionic surfactants such as sodium alkylbenzenesulfonates and sodium lauryl sulfate.

DE-A 43 04 066 describes a preparation with a content of 12% by weight of sodium lauryl ether sulfate and 3% by weight of sodium cocoyl glutamate. However, the subject-matter of this specification is the use of electrolytes for preventing the penetration of the surface-active substances present in the cleansing compositions and/or other substances present in these cleansing compositions into the external layers of the skin—in the preparation mentioned above, 8% by weight of sodium chloride are also present to whose presence the person skilled in the art attributes the reduction in the irritancy potential of the sodium lauryl ether sulfate.

The acylamino acids (where, within the scope of the present disclosure, the acylpeptides are also classed as acylamino acids) or salts thereof may advantageously be chosen from the group 1. acyl glutamates, for example sodium acyl glutamates, di-TEA palmitoyl aspartate and sodium caprylic acid/ capric acid glutamate,
2. acyl peptides, for example palmitoyl-hydrolyzed milk protein, sodium cocoyl-hydrolyzed soy protein and sodium/potassium cocoyl-hydrolyzed collagen,
3. sarcosinates, for example myristoyl sarcosine, TEA lauroylsarcosinate, sodium lauroylsarcosinate and sodium cocoylsarcosinate,
4. taurates, for example sodium lauroyl taurate and sodium methyl cocoyl taurate,
5. acyl lysinates, for example lauroyl lysine
6. acyl alaninates
7. acyl glycinates Also, the cosurfactants below may have an advantageous effect:

1. cocamidopropyl betaine
2. decyl polyglucoside
3. dodecyl polyglucoside
4. disodium laureth sulfosuccinate
5. sodium lauroyl sarcosinate
6. trilaureth 4-phosphate
7. sodium cocoamphoacetate
8. disodium cocoamphoacetate.

For the purposes of the present invention, it is particularly advantageous to use, as acylamino acid or salts thereof, acylglutamic acid, or acyl glutamates, in particular sodium acyl glutamates, which are characterized by the following structures:

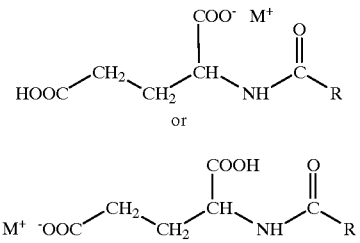

Of the sodium acyl glutamates in turn, sodium cocoyl glutamate, sodium lauroyl glutamate, sodium myristoyl glutamate, sodium stearoyl glutamate and sodium tallowyl glutamate have proven particularly advantageous.

Apart from the abovementioned surfactants, the compositions optionally comprise, according to the invention, the additives customary in cosmetics, for example perfumes, dyes, antimicrobial substances, refatting agents, complexing and sequestering agents, pearlizing agents, plant extracts, vitamins, active ingredients, preservatives, bactericides, pigments which have a coloring action, thickeners, emollients, moisturizers and/or humectants, fats, oils, waxes or other customary constituents of a cosmetic or dermatological formulation, such as alcohols, polyols, polymers, foam stabilizers, electrolytes, organic solvents or silicone derivatives.

The examples below serve to illustrate the present invention without limiting it. Unless stated otherwise, all amounts, proportions and percentages are by weight, based on the weight and the total amount or on the total weight of the preparations.

EXAMPLE 1

|  | % by weight |
|---|---|
| Sodium laureth sulfate (27.5% strength solution) | 48.00 |
| Cocoamidopropylbetaine (33% strength solution) | 5.00 |
| Sodium cocoyl glutamate (25% strength solution) | 5.00 |
| PEG-40 hydrogenated castor oil | 0.50 |
| PEG-100 hydrogenated glyceryl palmitate | 0.50 |
| Sodium benzoate | 0.45 |
| Sodium salicylate | 0.20 |
| Citric acid | 0.50 |
| Perfume | q.s. |
| Water | ad 100.00 |

The constituents are combined at room temperature and stirred to give a homogeneous mixture.

EXAMPLE 2

|  | % by weight |
|---|---|
| Sodium laureth sulfate (27.5% strength solution) | 40.00 |
| Cocoamidopropylbetaine (33% strength solution) | 10.00 |
| Sodium cocoyl glutamate (25% strength solution) | 8.00 |
| PEG-40 hydrogenated castor oil | 0.50 |
| PEG-100 hydrogenated glyceryl palmitate | 0.50 |
| Sodium benzoate | 0.45 |
| Sodium salicylate | 0.20 |
| Citric acid | 0.50 |
| Perfume | q.s. |
| Water | ad 100.00 |

The constituents are combined at room temperature and stirred to give a homogeneous mixture.

EXAMPLE 3

|  | % by weight |
|---|---|
| Sodium laureth sulfate (27.5% strength solution) | 30.00 |
| Cocoamidopropylbetaine (33% strength solution) | 15.00 |
| Sodium cocoyl glutamate (25% strength solution) | 4.50 |
| PEG-40 hydrogenated castor oil | 0.50 |
| PEG-100 hydrogenated glyceryl palmitate | 0.50 |
| Sodium benzoate | 0.45 |
| Sodium salicylate | 0.20 |
| Citric acid | 0.50 |
| Perfume | q.s. |
| Water | ad 100.00 |

The constituents are combined at room temperature and stirred to give a homogeneous mixture.

EXAMPLE 4

|  | % by weight |
|---|---|
| Sodium laureth sulfate (27.5% strength solution) | 43.00 |
| Cocoamidopropylbetaine (33% strength solution) | 11.00 |
| Sodium cocoyl glutamate (25% strength solution) | 4.50 |
| Decyl glucoside (50% strength solution) | 2.00 |
| PEG-40 hydrogenated castor oil | 0.50 |
| PEG-100 hydrogenated glyceryl palmitate | 0.50 |
| Sodium benzoate | 0.45 |
| Sodium salicylate | 0.20 |
| Citric acid | 0.50 |
| Perfume | q.s. |
| Water | ad 100.00 |

The constituents are combined at room temperature and stirred to give a homogeneous mixture.

EXAMPLE 5

|  | % by weight |
|---|---|
| Sodium laureth sulfate (27.5% strength solution) | 35.00 |
| Cocoamidopropylbetaine (33% strength solution) | 8.00 |
| Sodium cocoyl glutamate (25% strength solution) | 5.00 |
| Decyl glucoside (50% strength solution) | 4.00 |
| PEG-40 hydrogenated castor oil | 0.50 |
| PEG-100 hydrogenated glyceryl palmitate | 0.50 |
| Sodium benzoate | 0.45 |
| Sodium salicylate | 0.20 |
| Citric acid | 0.50 |
| Perfume | q.s. |
| Water | ad 100.00 |

The constituents are combined at room temperature and stirred to give a homogeneous mixture.

EXAMPLE 6

|  | % by weight |
|---|---|
| Sodium laureth sulfate (27.5% strength solution) | 25.00 |
| Cocoamidopropylbetaine (33% strength solution) | 14.00 |
| Sodium cocoyl glutamate (25% strength solution) | 6.00 |
| Decyl glucoside (50% strength solution) | 3.00 |
| PEG-40 hydrogenated castor oil | 0.50 |
| PEG-100 hydrogenated glyceryl palmitate | 0.50 |
| Sodium benzoate | 0.45 |
| Sodium salicylate | 0.20 |
| Citric acid | 0.50 |
| Perfume | q.s. |
| Water | ad 100.00 |

The constituents are combined at room temperature and stirred to give a homogeneous mixture.

EXAMPLE 7

|  | % by weight |
|---|---|
| Sodium laureth sulfate (27.5% strength solution) | 47.00 |
| Sodium cocoamphoacetate (36% strength solution) | 9.00 |
| Sodium cocoyl glutamate (25% strength solution) | 6.00 |
| PEG-40 hydrogenated castor oil | 0.50 |

-continued

| | % by weight |
|---|---|
| PEG-100 hydrogenated glyceryl palmitate | 0.50 |
| Sodium benzoate | 0.45 |
| Sodium salicylate | 0.20 |
| Citric acid | 0.50 |
| Perfume | q.s. |
| Water | ad 100.00 |

The constituents are combined at room temperature and stirred to give a homogeneous mixture.

EXAMPLE 8

| | % by weight |
|---|---|
| Sodium laureth sulfate (27.5% strength solution) | 41.00 |
| Sodium cocoamphoacetate (36% strength solution) | 6.50 |
| Sodium cocoyl glutamate (25% strength solution) | 7.50 |
| PEG-40 hydrogenated castor oil | 0.50 |
| PEG-100 hydrogenated glyceryl palmitate | 0.50 |
| Sodium benzoate | 0.45 |
| Sodium salicylate | 0.20 |
| Citric acid | 0.50 |
| Perfume | q.s. |
| Water | ad 100.00 |

The constituents are combined at room temperature and stirred to give a homogeneous mixture.

EXAMPLE 9

| | % by weight |
|---|---|
| Sodium laureth sulfate (27.5% strength solution) | 41.00 |
| Sodium cocoamphoacetate (36% strength solution) | 6.50 |
| Sodium lauroyl glutamate (25% strength solution) | 5.50 |
| PEG-40 hydrogenated castor oil | 0.50 |
| PEG-100 hydrogenated glyceryl palmitate | 0.50 |
| Sodium benzoate | 0.45 |
| Sodium salicylate | 0.20 |
| Citric acid | 0.50 |
| Perfume | q.s. |
| Water | ad 100.00 |

The constituents are combined at room temperature and stirred to give a homogeneous mixture.

EXAMPLE 10

| | % by weight |
|---|---|
| Sodium laureth sulfate (27.5% strength solution) | 32.00 |
| Sodium cocoamphoacetate (36% strength solution) | 5.00 |
| Sodium cocoyl glutamate (25% strength solution) | 5.00 |
| PEG-40 hydrogenated castor oil | 0.50 |
| PEG-100 hydrogenated glyceryl palmitate | 0.50 |
| Sodium benzoate | 0.45 |
| Sodium salicylate | 0.20 |
| Citric acid | 0.50 |
| Perfume | q.s. |
| Water | ad 100.00 |

The constituents are combined at room temperature and stirred to give a homogeneous mixture.

What is claimed is:

1. A method for reducing the binding of a sodium lauryl ether sulfate surfactant to the surface of the skin that comprises:
   selecting a co-surfactant which decreases or prevents binding by mixing a co-surfactant with the sodium lauryl ether sulfate surfactant before contacting the sodium lauryl ether sulfate surfactant with the surface of the skin,
   wherein the co-surfactant is not sodium lauryl ether sulfate surfactant and
   wherein the co-surfactant binds to the surface of the skin, thus achieving a predetermined decrease in or prevention of the binding of the sodium lauryl ether sulfate surfactant to the surface of the skin.

2. A method for preparing a mild washing-active cosmetic or dermatological preparation that comprises:
   selecting a cc-surfactant which decreases or prevents binding by mixing a co-surfactant with an anionic sodium lauryl ether sulfate surfactant to form a mild washing-active cosmetic or dermatological preparation,
   wherein the co-surfactant is not anionic sodium lauryl ether sulfate and
   wherein the co-surfactant binds to the surface of the skin, thus achieving a predetermined decrease in or prevention of the binding of the sodium lauryl ether sulfate surfactant to the surface of the skin when the preparation is applied to the skin.

3. The method according to claim 1, wherein the co-surfactant is selected from the group consisting of anionic N-acylamino acids, salts of anionic N-acylamino acids, and mixtures thereof.

4. The method according to claim 3, wherein the co-surfactant is selected from the group consisting of acyl glutamates, acyl peptides, sarcosinates, taurates, acyl lysinates, acyl alaninates, acyl glycinates, betaines, amphoacetates, polyglucosides, and sulfosuccinates.

5. The method according to claim 3, wherein the co-surfactant is trilaureth-4 phosphate.

6. The method according to claim 4, wherein the co-surfactant is selected from the group consisting of sodium acyl glutamate, di-TEA palmitoyl aspartate, sodium caprylic acid, capric acid glutamate, and mixtures thereof.

7. The method according to claim 4, wherein the co-surfactant is selected from the group consisting of palmitoyl-hydrolyzed milk protein, sodium cocoyl-hydrolyzed soy protein, sodium cocoyl-hydrolyzed collagen, potassium cocyl-hydrolyzed collagen, and mixtures thereof.

8. The method according to claim 4, wherein the co-surfactant is selected from the group consisting of myristoyl sarcosine, TEA lauroyl sarcosinate, sodium lauroyl sarcosinate, sodium cocoyl sarcosinate, and mixtures thereof.

9. The method according to claim 4, wherein the co-surfactant is selected from the group consisting of sodium lauroyl taurate, sodium methyl cocoyl taurate, and mixtures thereof.

10. The method according to claim 4, wherein the co-surfactant is lauroyl lysine.

11. The method according to claim 4, wherein the co-surfactant is an acyl alaninate or mixture thereof.

12. The method according to claim 4, wherein the co-surfactant is an acyl glycinate or mixture thereof.

13. The method according to claim 4, wherein the co-surfactant is a cocamidopropylbetaine or mixture thereof.

14. The method according to claim 4, wherein the co-surfactant is selected from the group consisting of sodium cocoamphoacetate, disodium cocoamphoacetate, or mixtures thereof.

15. The method according to claim 4, wherein the co-surfactant is selected from the group consisting of decyl polyglucosides, dodecyl polyglucosides, or mixtures thereof.

16. The method according to claim 4, wherein the co-surfactant is disodium lauroyl sulfosuccinate.

* * * * *